(12) United States Patent
Ogasawara et al.

(10) Patent No.: US 9,235,884 B2
(45) Date of Patent: Jan. 12, 2016

(54) INSPECTING APPARATUS AND INSPECTING METHOD OF ABSORBENT SHEET-LIKE MEMBER RELATED TO ABSORBENT ARTICLE

(75) Inventors: Yoshikazu Ogasawara, Kagawa (JP); Miwa Iida, Kagawa (JP)

(73) Assignee: Unicharm Corporation, Ehime (JP)

( * ) Notice: Subject to any disclaimer, the term of this patent is extended or adjusted under 35 U.S.C. 154(b) by 21 days.

(21) Appl. No.: 14/239,031

(22) PCT Filed: Aug. 22, 2012

(86) PCT No.: PCT/JP2012/005255
§ 371 (c)(1),
(2), (4) Date: Feb. 14, 2014

(87) PCT Pub. No.: WO2013/031143
PCT Pub. Date: Mar. 7, 2013

(65) Prior Publication Data
US 2014/0169632 A1 Jun. 19, 2014

(30) Foreign Application Priority Data

Aug. 30, 2011 (JP) ................................. 2011-187445

(51) Int. Cl.
*G06K 9/00* (2006.01)
*G06T 7/00* (2006.01)
*A61F 13/15* (2006.01)

(52) U.S. Cl.
CPC ......... *G06T 7/0008* (2013.01); *A61F 13/15658* (2013.01); *A61F 13/15772* (2013.01); *A61F 2013/1578* (2013.01)

(58) Field of Classification Search
None
See application file for complete search history.

(56) References Cited
U.S. PATENT DOCUMENTS

| 5,790,694 | A |  | 8/1998 | Maruo |
| 2003/0169433 | A1 |  | 9/2003 | Koele et al. |
| 2008/0240541 | A1 | * | 10/2008 | Chiou et al. ................. 382/141 |
| 2009/0123032 | A1 | * | 5/2009 | Kanisawa et al. ............ 382/106 |

FOREIGN PATENT DOCUMENTS

| JP | 63-283777 | 11/1988 |
| JP | 10-38541 | 2/1998 |
| JP | 2007-256162 A | 10/2007 |

(Continued)

OTHER PUBLICATIONS

International Search Report from corresponding PCT application No. PCT/JP2012/005255 dated Nov. 20, 2012 (1 pg).

(Continued)

*Primary Examiner* — Nirav G Patel
(74) *Attorney, Agent, or Firm* — Brinks Gilson & Lione

(57) ABSTRACT

An inspecting apparatus is provided which inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material. The inspecting apparatus includes: an imaging process section which is adapted to image, from one side of a surface of the absorbent sheet-like member, a region on the absorbent sheet-like member where the absorbent body is expected to exist, and that is adapted to produce data relating to a planar image of the region as planar image data of the absorbent body; an extracting process section which is adapted to extract a proper quantity region from the planar image by performing a binarization process on the produced planar image data based on a threshold value, the proper quantity region being an imaged region in which the liquid absorbent particulate is of a specified amount or more; and a pass/fail determination process section that is adapted to perform a pass/fail determination process based on a value indicating a size of the proper quantity region.

10 Claims, 7 Drawing Sheets

(56) References Cited

FOREIGN PATENT DOCUMENTS

| JP | 2008-154964 A | 7/2008 |
| JP | 2010-220768 A | 10/2010 |

OTHER PUBLICATIONS

European Supplementary Search Report from corresponding European application No. 12828173.0 dated Apr. 9, 2015 (6 pgs).

* cited by examiner

B-B CROSS-SECTIONAL VIEW

INSPECTING APPARATUS AND INSPECTING METHOD OF ABSORBENT SHEET-LIKE MEMBER RELATED TO ABSORBENT ARTICLE

RELATED APPLICATION

The present application is a 35 U.S.C. §371 national stage filing of International Patent Application No. PCT/JP2012/005255, filed Aug. 22, 2012, to which priority is claimed under 35 U.S.C. §120 and through which priority is claimed under 35 U.S.C. §119 to Japanese Priority Patent Application No. 2011-187445, filed Aug. 30, 2011.

TECHNICAL FIELD

The present invention relates to an inspecting apparatus and an inspecting method of an absorbent sheet-like member related to an absorbent article such as a disposable diaper.

BACKGROUND ART

Disposable diapers, incontinence pads and the like are known as examples of absorbent articles that absorb liquid such as liquid excretions. These absorbent articles typically include absorbent bodies made of liquid absorbent fibers, such as pulp fibers, formed into a predetermined shape.

However, recently, there are cases where a superabsorbent polymer (hereinafter, also referred to as SAP) in a particulate form is used as the main material of the absorbent body and liquid absorbent fibers are not used, or, if used, are used in an auxiliary manner.

An example of an apparatus that manufactures such an absorbent body is disclosed in PTL 1. With such an apparatus, the absorbent body is formed at a predetermined pitch in the transport direction by dropping and depositing the SAP at intervals on a continuous web which is transported in the transport direction.

On the other hand, PTL 2 discloses a method of measuring an amount of SAP that is scattered at intervals on an absorbent body which has pulp fibers as its main material. More specifically, a capacitance-based sensor is provided at a predetermined position in the transport direction of the absorbent body, and a distribution of the amount of SAP in the transport direction is measured based on a change of capacitance while the absorbent body is passing below the sensor.

CITATION LIST

Patent Literature

[PTL 1]
JP-A-H63-283777
[PTL 2]
JP-A-2008-154964

SUMMARY OF INVENTION

Technical Problem

As has been described above, in a case where the absorbent body includes SAP as a main material, its absorbing capacity substantially depends on SAP. Therefore, if SAP is deposited with a distribution that is unintentionally greatly deviated either in the transport direction or in the width direction, liquid cannot be absorbed at a portion where the liquid should be absorbed when worn, and thus a function which should be essentially fulfilled by the absorbent body is greatly reduced. Also, even if SAP exists, a planned absorption capacity cannot be achieved at a portion where it exists with a basis weight ($g/m^2$) which is much lower than the planned value.

Therefore, from a quality management point of view, it is preferable to check whether the SAP exists with a specified basis weight or more for substantially the entire region in both the transport direction and the width direction, and there is a need to provide an inspection apparatus or an inspection method capable of performing such a check.

However, with the known measurement method of the above-mentioned PTL 2, a distribution of an amount of SAP in the transport direction can be measured, but a distribution in a width direction which is orthogonal to the transport direction cannot be measured, and the above-described need cannot be satisfied.

Accordingly, the present invention has been made in view of such a problem and its object is to determine whether or not a liquid absorbent particulate is deposited with a specific basis weight or more throughout a predetermined region of a predetermined deposition pattern in an inspection apparatus or an inspection method of an absorbent sheet-like member including a continuous web transported along a transport direction and an absorbent body formed at intervals in the transport direction on one side of the continuous web and with liquid absorbent particulate being a main material.

Solution to Problem

In order to achieve the objects described above, the main aspect of the present invention is:

an inspecting apparatus which inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting apparatus including:

an imaging process section which is adapted to image, from one side of a surface of the absorbent sheet-like member, a region on the absorbent sheet-like member where the absorbent body is expected to exist, and that is adapted to produce data relating to a planar image of the region as planar image data of the absorbent body;

an extracting process section which is adapted to extract a proper quantity region from the planar image by performing a binarization process on the produced planar image data based on a threshold value, the proper quantity region being an imaged region in which the liquid absorbent particulate is of a specified amount or more; and a pass/fail determination process section that is adapted to perform a pass/fail determination process based on a value indicating a size of the proper quantity region.

Further provided is an inspecting method which inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting method including:

imaging, from one side of a surface of the absorbent sheet-like member, a region on the absorbent sheet-like member where the absorbent body is expected to exist, and producing data relating to a planar image of the region as planar image data of the absorbent body;

extracting a proper quantity region from the planar image by performing a binary process on the produced planar image data based on a threshold value, the proper quantity region being an imaged region in which the liquid absorbent particulate is of a specified amount or more; and performing a pass/fail determination process based on a value indicating the size of the proper quantity region.

Other features of the present invention will be elucidated from the disclosures in the specification and accompanying drawings.

Advantageous Effects of Invention

According to an aspect of the invention, it is possible to measure whether or not a liquid absorbent particulate is deposited for a specific quantity or more throughout a predetermined region of the deposition pattern.

DESCRIPTION OF EMBODIMENTS

Figure 1:
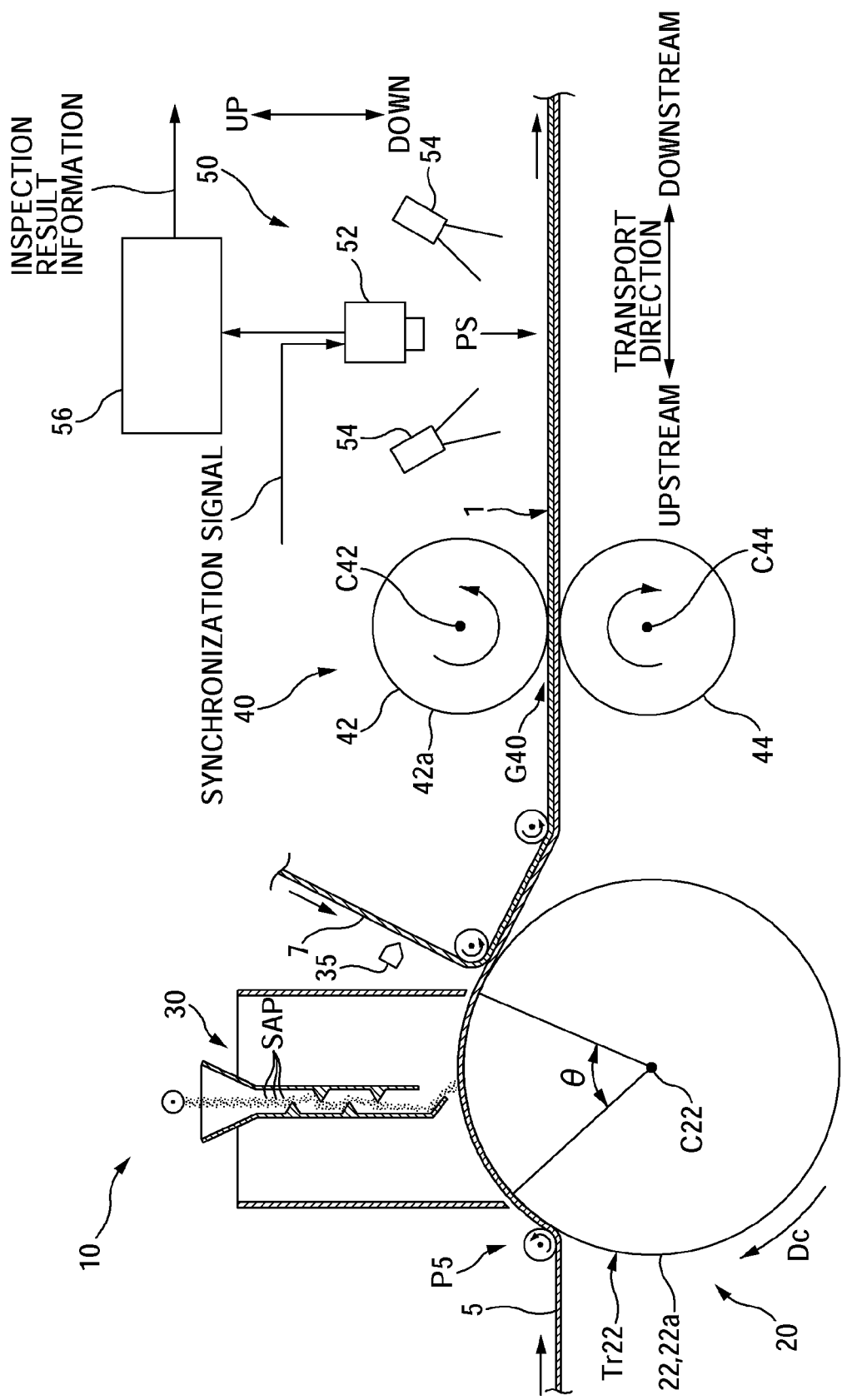
FIG. 1 is a schematic side view of an inspecting apparatus 50 of the present embodiment.

At least the following matters will be disclosed in the present specification and accompanying drawings.

The present invention is an inspecting apparatus that inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting apparatus including:

an imaging process section which is adapted to image, from one side of a surface of the absorbent sheet-like member, a region on the absorbent sheet-like member where the absorbent body is expected to exist, and that is adapted to produce data relating to a planar image of the region as planar image data of the absorbent body;

an extracting process section which is adapted to extract a proper quantity region from the planar image by performing a binarization process on the produced planar image data based on a threshold value, the proper quantity region being an imaged region in which the liquid absorbent particulate is of a specified amount or more; and a pass/fail determination process section that is adapted to perform a pass/fail determination process based on a value indicating a size of the proper quantity region.

With such an inspecting apparatus of an absorbent sheet-like member for forming an absorbent article, in performing a binarizing process of an imaged and produced planar image data of an absorbent body, an imaged region in which the above-mentioned absorbent particulate has a specified basis weight or more is extracted as a proper quantity region, and a pass/fail determination of the absorbent body is performed based on a value indicating a size, e.g., an area, of the extracted proper quantity region. Therefore, throughout a predetermined range in a region specified by the deposition pattern of the absorbent body where the liquid absorbent particulate is expected to exist, it becomes possible to determine whether the liquid absorbent particulate is deposited with a specified basis weight or more.

It is preferable that, with such an inspecting apparatus which inspects an absorbent sheet-like member relating to an absorbent article, the absorbent sheet-like member is provided with a plurality of particulate deposition target regions for each absorbent body based on the deposition pattern, the particulate deposition target regions being arranged discretely in an island-like manner, each of the particulate deposition target regions being a region in which the liquid absorbent particulate is expected to exist, the extracting process section sets respective inspection windows for at least some of the plurality of particulate deposition target regions and is adapted to extract the proper quantity region for each inspection window, the inspection window having a contour substantially corresponding to a contour of the particulate deposition target region, and the pass/fail determination process section is adapted to perform a pass/fail determination of the absorbent body based on a value indicating the size of the proper quantity region which has been extracted for each inspection window.

With such an inspecting apparatus of an absorbent sheet-like member relating to an absorbent article, an inspection window having a contour shape substantially corresponding to a contour shape of a particulate deposition target region, i.e., a region in which the liquid absorbent particulate is expected to exist, is set for each of the particulate deposition target regions for some of the plurality of the particulate deposition target regions, and for each window, a proper quantity region is extracted that is a region in which the liquid absorbent particulate of a specific basis weight or more is imaged. In other words, for some of the plurality of particulate deposition target regions, a proper quantity region is extracted for each of these particulate deposition target regions. Then, based on a value indicating a size of each of the extracted proper amount regions, a pass/fail determination of the absorbent body is performed. Thus, whether or not there is a deviation in a deposition pattern can be reflected in the pass/fail determination of the absorbent body, and therefore, determination of whether or not SAP is deposited with a specified basis weight or more throughout a predetermined range of the deposition pattern can be performed in a more accurate manner.

It is preferable that, with such an inspecting apparatus which inspects an absorbent sheet-like member relating to an absorbent article, the extracting process section sets an inspection window for each of the particulate deposition target regions and is adapted to extract the proper quantity region for each inspection window, the inspection window having a contour substantially corresponding to a contour of the particulate deposition target region, and the pass/fail determination process section is adapted to perform a pass/fail determination of the absorbent body based on a value indicating the size of the proper quantity region which has been extracted for each inspection window.

With such an inspecting apparatus of an absorbent sheet-like member relating to an absorbent article, an inspection window of a contour shape substantially corresponding to a contour shape of a particulate deposition target region is set for each of the particulate deposition target regions, and a proper quantity region, which is a region in which the liquid absorbent particulate of a specific basis weight or more is imaged for each inspection window, is extracted. In other words, the proper quantity region is extracted for each of the particulate deposition target regions and for all the particulate deposition target regions. Then, based on a value indicating a size of each of the extracted proper quantity regions, a pass/fail determination of the absorbent body is performed. Therefore, whether or not there is a deviation in a deposition pattern can be reflected in the pass/fail determination of the absorbent body, and therefore, determination of whether or not SAP is deposited with a specified basis weight or not throughout a predetermined range of the deposition pattern can be performed in a more accurate manner.

It is preferable that, with such an inspecting apparatus which inspects an absorbent sheet-like member relating to an absorbent article, wherein, the extracting process section has a numerical value for at least one of hue, brightness and saturation, that serve as the threshold value, and the extracting process section is adapted to extract the proper quantity region from the planar image by performing a binarization process on the planar image data based on the threshold value.

With such an inspecting apparatus of an absorbent sheet-like member relating to an absorbent article, a numerical value of at least one of hue, brightness and saturation serves as the threshold value for the binarization process, and the region that has been imaged with the liquid absorbent particles of a prescribed basis weight or more can be certainly extracted.

It is preferable that, with such an inspecting apparatus which inspects an absorbent sheet-like member relating to an absorbent article, the planar image data is grey scale data.

With such an inspecting apparatus of an absorbent sheet-like member relating to an absorbent article, the planar image data used for the binarization process is grey scale data, so that the data amount can be made small. As a result, in the case of storing the planar image data in respect to the binarization process, even a small capacity memory can handle it, and the inspection apparatus can be made at a low cost.

It is preferable that, with such an inspecting apparatus which inspects an absorbent sheet-like member relating to an absorbent article, the extracting process section has a numerical value for brightness, that serves as the threshold value.

With such an inspecting apparatus of an absorbent sheet-like member relating to an absorbent article, a numeral value of brightness serves as the threshold value. Thus, from the grey scale planar image data, the region imaged with the liquid absorbent particles of a prescribed basis weight or more can be smoothly extracted.

It is preferable that, with such an inspecting apparatus which inspects an absorbent sheet-like member relating to an absorbent article, the planar image data is color image data, the extracting process section has numerical value ranges for hue, brightness and saturation, respectively, that serve as the threshold value, and the extracting process section is adapted to extract the proper quantity region from the planar image by performing a color binarization process on the planar image data based on the threshold value.

With such an inspecting apparatus of an absorbent sheet-like member relating to an absorbent article, respective numerical value ranges of hue, brightness and saturation relating to a threshold used in a color binarization process can be set so as to correspond to a specific color (a color that is specific to a region in which a liquid absorbent particulate of a specified basis weight or more is imaged) when a region in which the liquid absorbent particulate exists is seen from an image processing section side. Thus, accordingly, an extracting efficiency of the proper quantity region in which the liquid absorbent particulate exists can be improved.

It is preferable that, with such an inspecting apparatus which inspects an absorbent sheet-like member relating to an absorbent article, the absorbent sheet-like member has another continuous web that is overlaid on the continuous web so as to sandwich the absorbent bodies in a thickness direction, and the continuous webs are integrally joined with each other, at least in part, at a region other than the particulate deposition target region and the liquid absorbent particulate is enclosed between the continuous webs due to the joining at the region.

With such an inspecting apparatus of an absorbent sheet-like member relating to an absorbent article, it is possible to effectively inspect an absorbent sheet-like member in which a liquid absorbent particulate is enclosed to have an improved anti-leaking property of such a particulate. The continuous webs may be integrally joined with each other around each particulate desposition target region, this joining being partial or total.

It is preferable that, with such an inspecting apparatus which inspects an absorbent sheet-like member relating to an absorbent article, one of the group including the continuous web, the other continuous web and the liquid absorbent particulate, is colored with a color other than white, and the imaging process section is adapted to receive reflected light from the region of the absorbent sheet-like member where the absorbent body is expected to exist, and images the region.

With such an inspecting apparatus of an absorbent sheet-like member relating to an absorbent article, at least one of the continuous web, the other continuous web and the liquid absorbent particulate may be colored with a color other than white, but even in such a case, with the setting of each numerical value range of hue, brightness and saturation relating to the threshold of the color binarization process, an imaged region in which the liquid absorbent particulate is of a specified basis weight or more can be extracted without any problem.

It is preferable that with such an inspecting apparatus which inspects an absorbent sheet-like member relating to an absorbent article, the planar image data is produced for each of the absorbent bodies by imaging the planar image for each of the absorbent bodies.

With such an inspecting apparatus of an absorbent sheet-like member relating to an absorbent article, since the planar image data is produced for each absorbent body, all the absorbent bodies become targets of the inspection. In other words, a complete inspection is performed and, as a result, management accuracy of quality management can be improved.

Further provided is an inspecting method which inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting method including:

imaging, from one side of a surface of the absorbent sheet-like member, a region on the absorbent sheet-like member where the absorbent body is expected to exist, and producing data relating to a planar image of the region as planar image data of the absorbent body;

extracting a proper quantity region from the planar image by performing a binary process on the produced planar image data based on a threshold value, the proper quantity region being an imaged region in which the liquid absorbent particulate is of a specified amount or more; and performing a pass/fail determination process based on a value indicating the size of the proper quantity region.

With such an inspecting method of an absorbent sheet-like member relating to an absorbent article, in performing a binarizing process on an imaged and produced planar image data of an absorbent body with a threshold value, a region in which the liquid absorbent particulate has a specified basis weight or more is extracted as a proper quantity region, and a pass/fail determination of the absorbent body is performed based on a value, e.g., an area, indicating a size of the extracted proper quantity region. Therefore, through out a predetermined range of a region in which the liquid absorbent particulate specified by the deposition pattern of the absorbent body is expected to exist, it becomes possible to determine whether or not the liquid absorbent particulate is deposited with a specified basis weight or more.

Present Embodiment

Figure 2A:
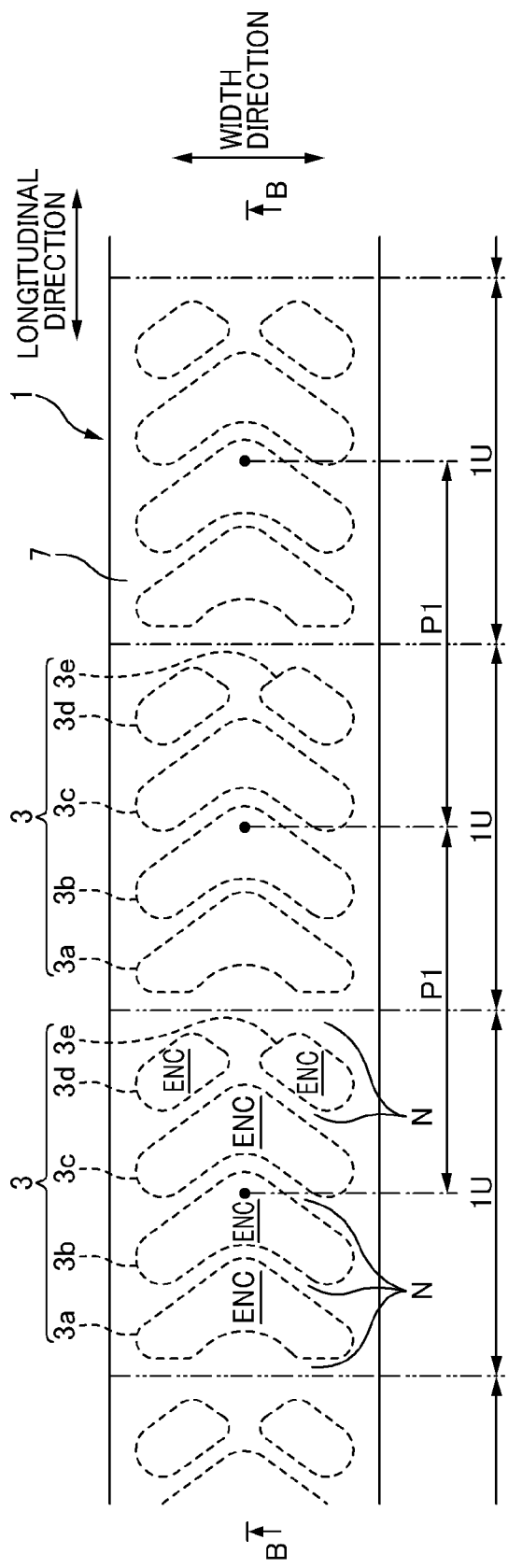
FIG. 2A illustrates a schematic plan view of an absorbent sheet-like member 1 to be inspected by the inspecting apparatus 50 and FIG. 2B is a cross-sectional view taken along B-B in FIG. 2A.
Figure 2B:
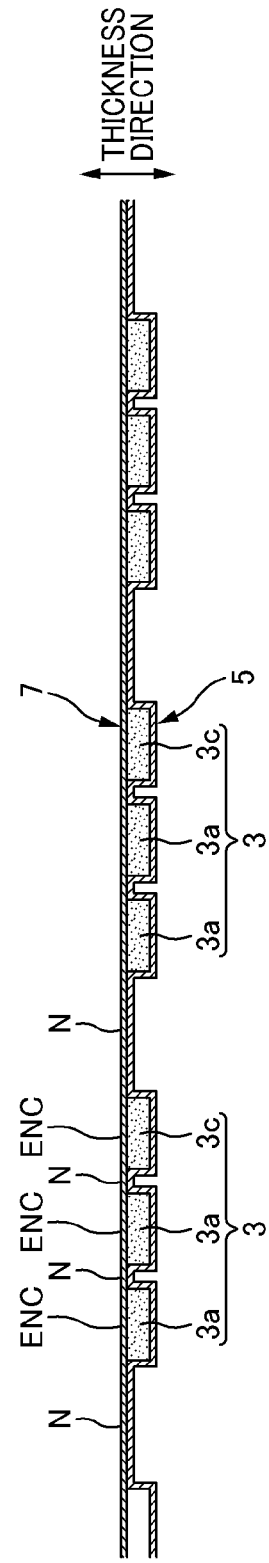

FIG. 1 is a schematic side view of an inspecting apparatus 50 of the present embodiment. FIG. 2A illustrates a schematic plan view of an absorbent sheet-like member 1 to be inspected by the inspecting apparatus 50 and FIG. 2B is a cross-sectional view taken along B-B in FIG. 2A. It is to be noted that, in FIG. 1, some of the structures are shown in a vertical cross sectional view.

The inspecting apparatus 50 is an apparatus that inspects the absorbent sheet-like member 1 which is provided as one of the components of a disposable diaper or an incontinence pad, for example. In other words, as shown in FIG. 1, the inspecting apparatus 50 is provided downstream of the manufacturing apparatus 10 of the absorbent sheet-like member 1, and inspects the absorbent sheet-like member 1 delivered from the manufacturing apparatus 10 for the deposition distribution (state of deposition) of the SAP for each absorbent body 3. Then, the information resulting from the inspection, which is either the information that the product is acceptable or the information that the product is defective, is linked to the relevant unit 1U of the absorbent sheet-like member 1 corresponding to each absorbent body 3, i.e., each unit 1U of the absorbent sheet-like member 1 corresponding to a single-cut sheet-like product 1U shown in FIG. 2A. Then, the relevant information resulting from the inspection is provided for a subsequent process, such as a downstream process in which a defective product is ejected from the production line.

Absorbent Sheet-Like Member 1

As shown in FIG. 2A, a planar shape of the single-cut sheet-like product 1U of the absorbent sheet-like member 1 is a substantially rectangular shape, in this example, having a longitudinal direction and a width direction. As shown in FIG. 2B, this example has a substantially three layered structure in a thickness direction. To be more specific, the absorbent body 3 that absorbs a liquid is covered with a front face web 5 from a front face side, which is a human body side (ie a side which is adapted to lie adjacent the crotch region of a human body for absorbing excreted waste), and is covered with a back face web 7 from a back face side, which is a side opposite to the human body side. Then, with the absorbent body 3 being sandwiched between the front face web 5 and the back face web 7, both of these webs 5 and 7 are joined at least at a portion extending outwards from a peripheral edge of the absorbent body 3, and thus the single-cut sheet-like product 1U of the absorbent sheet-like member 1 is formed as an integrated body.

The front face web 5 and the back face web 7 are webs having an appropriate liquid permeability and are, for example, nonwoven fabrics having a basis weight of 10-50 g/m$^2$ made of, for example, synthetic fiber. The synthetic fiber may be a composite fiber of a sheath-core structure or a single fiber, such as polyethylene and polyethylene terephthalate. It is to be noted that the back face web 7 may be a liquid impermeable web.

The absorbent body 3 includes many particles of superabsorbent polymer (hereinafter also referred to as SAP), preferably having a particle size of 100-800 microns, as an example of a liquid absorbent particulate and as a main material, and the particles of SAP are deposited with a basis weight of, for example, 100-500 g/m$^2$. SAP is an absorbent high molecular weight polymer having a three dimensional mesh structure in which water soluble polymers are moderately cross-linked. It absorbs water hundreds times to a thousand times its volume prior to the absorbing of water, and it is basically insoluble in water, and the water which has been absorbed is not released even under a certain pressure. Such a SAP may include a starch-based SAP, an acrylic acid-based SAP or an amino acid-based SAP, and an example of a product is UG-840D (product name, manufactured by Sumitomo Seika Chemicals Co., Ltd.). Also, in this example, the absorbent body 3 is made of SAP only, but a liquid absorbent fiber such as a pulp fiber may be mixed in as an auxiliary absorbent material. The main material means the material type having the greatest liquid absorbing ability in terms of the amount (volume amount) of liquid absorbed, among the types of material constituting the absorbent body 3.

As can be seen in FIG. 2A, the absorbent body 3 includes a plurality of island shaped deposited bodies 3a, 3b, 3c, 3d and 3e that are discretely divided into a predetermined deposition pattern PT. In the illustrated example, the three deposited bodies 3a, 3b and 3c, each having a V-shaped contour when seen in a plan view, are arranged in such a manner that the respective bent portions are aligned at a central position in the width direction of the absorbent sheet-like member 1 and a pointing direction of the V-shape is oriented rearwards in the longitudinal direction. At a position closer to the rear end than the three deposited bodies 3a, 3b and 3c in the longitudinal direction, a pair of right and left deposited bodies 3d and 3e are arranged which are separated in the width direction with the bent portion being removed. Thus, the absorbent body 3 includes a total of five deposited bodies 3a to 3e. Each deposited body 3a, 3b, . . . 3e is enclosed by a portion of the front face web 5 and a portion of the back face web 7 that covers each deposited body 3a, 3b, . . . 3e in such a manner that the SAP belonging thereto does not move to/from the other deposited bodies. In other words, at a portion N of the front face web 5 and the back face web 7 where there are no overlaid or underlying deposited bodies 3a-3e, as appropriate, the front face web 5 and the back face web 7 are joined by welding or the like, and thus each deposited body 3a, 3b . . . 3e is enclosed by a portion of the front face web 5 and a portion of the back face web 7 covering each deposited body 3a, 3b . . . 3e. Here, the portion of the front face web 5 and the portion of the back face web 7 covering each deposited body 3a, 3b . . . 3e are referred to as an "enclosed section ENC", and a portion of the front face web 5 and the back face web 7 where there is no deposited body 3a . . . 3e is also referred to as a "deposited-body-free portion N".

Further, in this example, in order to suppress movement of the SAP particles within the enclosed section ENC, an adhesive agent such as a hot-melt adhesive is applied to one or both of the front face web 5 and the back face web 7 at a region where the deposited bodies 3a to 3e are to be formed on the web, and thus the movement within the enclosed section ENC is restricted for those SAP particles that are located near the region where the adhesive is applied.

The single-cut sheet-like product 1U of such an absorbent sheet-like member 1 is, for example, arranged on the human body side surface of a diaper or an incontinence pad selectively at a location where the buttocks of a wearer make contact. When worn, each of the deposited bodies 3a, 3b . . . 3e can come into close contact with a gap between the right and left buttocks of the wearer in a facilitated manner based on the V-shaped configuration and the like of each of the deposited bodies 3a, 3b, . . . 3e, and as result, liquid excretions such as urine can be effectively prevented from leaking out.

Figure 3:
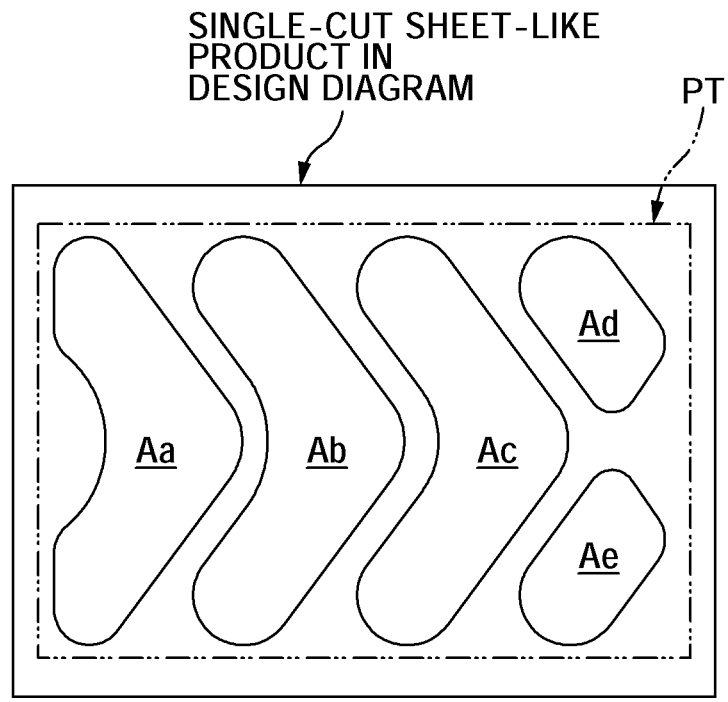
FIG. 3 is a layout of a single-cut sheet-like product 1 of the absorbent sheet-like member 1 in which a deposited pattern PT is defined.

It is to be noted that the above-mentioned deposition pattern PT is defined in the design diagram of the single-cut sheet-like product 1U of the absorbent sheet-like member 1 shown in FIG. 3. In other word, the deposition pattern PT indicates target regions Aa, Ab, Ac, Ad and Ae where the deposited bodies 3a to 3e are to be formed on the absorbent sheet-like member 1. Therefore, hereinafter, the regions Aa to Ae (theoretical region) where the deposited bodies 3a to 3e are to be formed based on the deposition pattern PT are also referred to as "SAP deposition target regions Aa to Ae".

It is also to be noted that the deposition pattern PT is not limited to five deposition pattern target regions; only one may be present; two, three or four may be present; more than five regions may be present. The SAP deposition target regions Aa to Ae may have any shape and so the invention is not limited to the shape shown and described herein. For example, SAP deposition target regions Aa to Ae may be rectangular, oval, square, triangular etc. It may be regular or irregular in shape.

Manufacturing Apparatus 10 of Absorbent Sheet-Like Member 1

As shown in FIG. 1, at a point immediately after the manufacturing of the absorbent sheet-like member 1, the absorbent sheet-like member 1 is not yet divided into single-cut sheet-like products 1U. In other words, the absorbent sheet-like member 1 is in a state of a continuous body where the single-cut sheet-like products 1U, aligned in the transport direction at a product pitch P1, are integrally connected. The width direction of the manufacturing apparatus 10 is parallel to the width direction (in FIG. 1, a direction penetrating the plane of paper) of the continuous sheet-like member 1 transported in the transport direction, and hereinafter, this width direction is also referred to as a "CD-direction". It is to be noted that CD-direction is horizontal.

The manufacturing apparatus 10 includes a rotating drum unit 20 and a heat sealing unit 40. Based on the above-mentioned deposition pattern PT, the rotating drum unit 20 forms deposited bodies 3a-3e of SAP, serving as the absorbent body 3, between a front face web 5 (corresponding to a continuous web) and a back face web 7 (corresponding to another web). The heat sealing unit 40 joins the front face web 5 and the back face web 7 by thermal welding at a deposition-body-free portion N and thus each deposited body 3a, 3b, . . . 3e is enclosed between the front face web 5 and the back face web 7. Then, the thus-produced absorbent sheet-like member 1 is sent to the inspecting apparatus 50 in a state where it is continuous in the transport direction. Hereinafter, the rotating drum unit 20 and the heat sealing unit 40 will be described.

Figure 4:
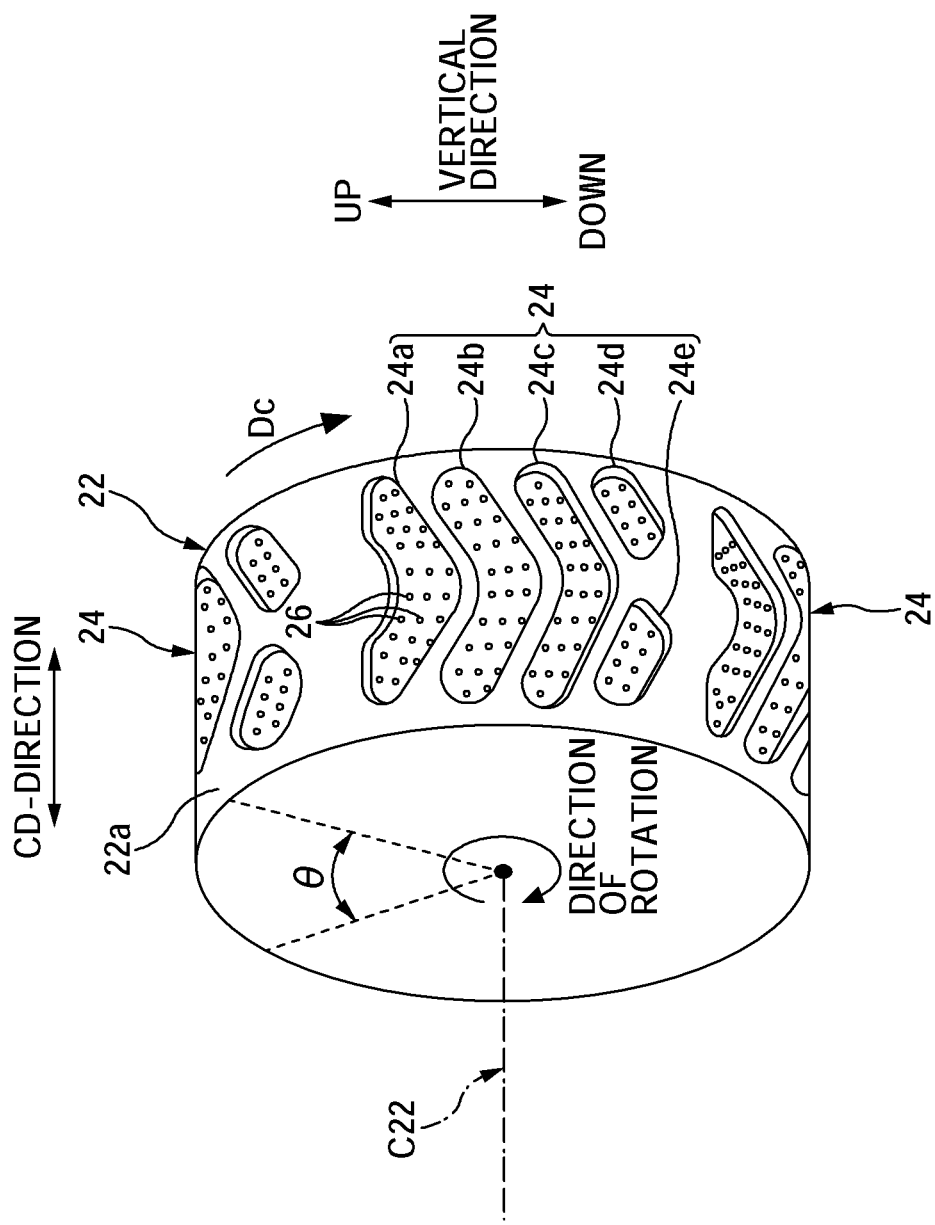
FIG. 4 is a schematic perspective view of a rotating drum 22 of a rotating drum unit 20.

The rotating drum unit 20 has a rotating drum 22. FIG. 4 is a schematic perspective view of the rotating drum 22. The rotating drum 22 has a main body which is a cylindrical member that is driven and rotates about a horizontal axis C22 extending along the CD-direction. Then, its outer peripheral surface 22a is provided with molds 24, 24, . . . , thereon at a predetermined pitch in the peripheral direction Dc of the rotating drum 22, the molds 24, 24, . . . , are for molding the absorbent body 3 by depositing the SAP by suction. Each mold 24 has five recessed sections 24a, 24b, 24c, 24d and 24e as suction sections in accordance with the above-mentioned deposition pattern PT. In other words, the recessed sections 24a, 24b . . . 24e correspond to the SAP deposition target regions Aa, Ab . . . Ae relating to the above-mentioned absorbent sheet-like member 1, respectively, and thus, the shape of a bottom surface of each of the recessed sections 24a, 24b, . . . , 24e is substantially the same as the shape of each of the corresponding SAP deposition target regions Aa, Ab . . . Ae. Also, the bottom surface of each of the recessed sections 24a, 24b, . . . , 24e is substantially horizontal with respect to the CD-direction and each of the bottom sections is further provided with a plurality of suction holes 26 formed therein.

Such a rotating drum 22 continuously rotates as shown in FIG. 1, and thus its outer peripheral surface 22a continuously moves along the predetermined circumferential track Tr22. A supplying position P5 for the front face web 5 is provided at a predetermined position P5 on the circumferential track Tr22 and, at the supplying position P5, the front face web 5 is supplied towards the outer peripheral surface 22a and wound at a predetermined winding angle θ. Then, the front face web 5 is transported in a substantially integral manner with the outer peripheral surface 22a. SAP is supplied towards the outer peripheral surface 22a of the rotating drum 22, where the front face web 5 is wound, by being dropped from the SAP supplying apparatus 30, and further, in parallel, the suction holes 26 of each recessed section 24a, 24b, . . . 24e of the outer peripheral surface 22a performs suction while restricting the passing of the SAP, and thus SAP is sucked across the front face web 5 and deposited onto each recessed section 24a, 24b, . . . 24e, and each deposited body 3a, 3b . . . 3e of the absorbent body 3 is formed.

Finally, the back face web 7 is supplied towards the front face web 5 that is being wound on the rotating drum 22, and layered onto the front face web 5. Before this merging, an adhesive agent is applied to substantially the entire surface of one of the surfaces of the back face web 7 by the adhesive applying unit 35. Therefore, these webs 5 and 7 are temporarily joined together with the absorbent body 3 being sandwiched between the front face web 5 and the back face web 7. Then, as a continuous body that continues in the transport direction in such a temporarily-joined state, the absorbent sheet-like member 1 is sent to the heat sealing unit 40.

The heat sealing unit 40 has, for example, a pair of upper and lower rolls 42, 44, and these rolls 42, 44 rotate about the respective horizontal axes C42, C42 that lie along the CD-direction, and along the transport direction at a peripheral speed that is the same as the transport speed of the absorbent sheet-like member 1. Further, at least one of the rolls 42 and 44 is a heated roll whose outer peripheral surface has been heated to a temperature sufficient for welding. Further, on an outer peripheral surface of the lower roll 44 that is one of the rolls 42 and 44, five recessed sections (not shown) are formed in correspondence with the five deposited bodies 3a, 3b . . . 3e, respectively, which are absorbent bodies 3 of the absorbent sheet-like member 1. Each of the recessed sections is formed to have a size slightly larger than the corresponding SAP deposition target region Aa, Ab . . . Ae in each of the CD-direction and the peripheral direction of the lower roll 44. Therefore, when the absorbent sheet-like member 1 passes through a roll gap G40 between the upper and lower rolls 42 and 44, the enclosed sections ENC of the deposited bodies 3a, 3b . . . 3e of the absorbent sheet-like member 1 (FIGS. 2A and 2B) respectively enter the corresponding recessed sections, and thus at the roll gap G40, the deposition-body-free portion N of the absorbent sheet-like member 1 (FIGS. 2A and 2B) is thermally welded in a selective manner by a portion surrounding each of the recessed sections of the lower roll 44 and the outer peripheral surface 42a of the upper roll 42, and thus the front face web 5 and the back face web 7 are completely welded. Then, the completely welded absorbent sheet-like member 1 is sent to the inspecting apparatus 50 in a continuous state in the transport direction.

Inspecting Apparatus 50 of Absorbent Sheet Member 1

As can be seen in FIG. 1, the inspecting apparatus 50 is arranged downstream of the heat sealing unit 40. The invention is not limited to this arrangement, as the inspecting apparatus 50 may be arranged upstream of the heat sealing unit 40, although the arrangement of FIG. 1 is more preferable than this arrangement. The inspecting apparatus 50 inspects, for each absorbent body 3 of the absorbent sheet-like member 1, whether or not SAP is properly deposited with the deposition pattern PT. In other words, it inspects, for each absorbent body 3 of the absorbent sheet-like member 1, whether or not SAP exists with a specified basis weight or more for substantially the entire region (corresponding to a predetermined region) in the SAP deposition target regions Aa, Ab, . . . Ae (corresponding to a particulate deposition target region) which are regions where the SAP should exist. For example, in the case where it is determined that the size of a region in which the SAP actually exists with the above-mentioned basis weight or more in the SAP deposition target regions Aa, Ab, . . . Ae is smaller than a pass/fail determination threshold which is a planned value and which will be described later, the single-cut sheet-like product 1U of the absorbent sheet-like member 1 provided with this absorbent body 3 is associated with the fact that it is a defective product such as by giving defective product information, and used for ejection of a defective product in a downstream step.

The inspecting apparatus 50 includes: a camera 52 serving as the imaging processing section that is provided at a predetermined position on the transport path of the absorbent sheet-like member 1; illuminating members 54, 54 that illuminate the imaging position PS on the transport path; and the image processing section 56.

The camera 52 is, for example, a CCD (charge coupled device) camera. It is arranged to oppose one surface of the absorbent sheet-like member 1 and performs imaging of one surface of the absorbent sheet-like member 1. The imaging operation is carried out based on a synchronization signal, and thus a region A3 on the surface of the absorbent sheet-like member 1 where the absorbent body 3 should exist is imaged in such a manner that the center of the plane CA3 of the region A3 substantially matches a center of the plane CP of the planar image (see FIG. 5). To be more specific, the synchronization signal is a rotation angle signal obtained by assigning each of the rotation angle values between 0° and 360° in proportion to the transport amount by taking the transport amount corresponding to a single piece of the single-cut sheet-like product 1U of the absorbent sheet-like member 1 (i.e., product pitch P1 (FIG. 2A)) as a unit transport amount. In other words, when a portion of the absorbent sheet-like member 1 corresponding to a single piece of the single-cut sheet-like product 1U is transported, a rotation angle value between 0° and 360° is outputted and, each time the transportation of a single piece is performed, the rotation angle value between 0° and 360° is outputted repeatedly and periodically. Therefore, by finding a phase of the synchronization signal corresponding to the imaging timing where the center of the plane CA3 of the region A3 and the center of the plane CP of the planar image matches, as has been described above, as a predetermined rotation angle value, and presetting an imaging operation such that it is performed at the predetermined rotation angle value which is its phase, imaging can be performed in such a manner that, for a portion corresponding to the single-cut sheet-like product 1U of all the absorbent sheet-like member 1 passing the imaging position PS thereafter, the center of the plane CA3 of the region A3 where the absorbent body 3 should exist matches with the center of the plane CP of the planar image, as described above.

Then, the camera 52 that is adjusted to such imaging timing performs imaging for each absorbent body 3 of the absorbent sheet-like member 1, and each time the imaging is performed, produces data on the imaged planar image as the planar image data. Then, each time the generating is performed, sends the planar image data to an image processing section 56. Then, at the image processing section 56, based on the planar image data, the pass/fail determination of the absorbent body 3 of the absorbent sheet-like member 1 is performed for each absorbent body 3, i.e., for each single-cut sheet-like product 1U of the absorbent sheet-like member 1. Accordingly, all of the single-cut sheet-like products 1U will be inspected. However, it is not limited thereto, and, for example, imaging may be carried out in such a manner that every other, every three, every four, etc. of the absorbent bodies 3 are imaged. In such a case, since the planar image data is produced for every other, every three, every four, etc. of the absorbent bodies 3, the pass/fail determination is carried out for every other, every three, every four, etc. of the absorbent bodies 3. In other words, a sampling inspection for the single-cut sheet-like products 1U is carried out for every other, every three, every four, etc. single-cut sheet-like products 1U. The pass/fail determination and the like will be described in detail later in the specification.

The illuminating member 54 is a suitable light such as, for example, a white LED light and an ultraviolet light, and the type of light source is suitably selected in accordance with the imaging condition of a scene. Also, during the imaging, a light-receiving condition, such as whether the light from the illuminating member 54 is to be received by the camera 52 as a transmission light, or to be received as a reflected light is suitably determined in accordance with the imaging condition of a scene. It is to be noted that, in the example shown in FIG. 1, the illuminating member 54 is arranged on the same side as the camera 52 with respect to one side of the absorbent sheet-like member 1, and thus the camera 52 receives light reflected on the other side of the absorbent sheet-like member 1.

The image processing section 56 has a suitable computer as a main body, and includes a processor and a memory. The processor reads out and executes various processing programs such as a binarizing process program pre-stored in the memory, and performs various processes such as a binarizing process.

In the image processing section 56, the binarizing process is performed on the transmitted planar image data, and extracts, from the planar image, a SAP-proper-quantity region that is a region in which SAP of the specified amount or more is imaged. Hereinafter, this is referred to as an "extracting process". Then, a pass/fail determination of the absorbent body 3 is performed by comparing the size of an area of the extracted SAP-proper-quantity region with the specified pass/fail determination threshold. Hereinafter, this is referred to as a "pass/fail determination process". It is to be noted that the SAP-proper-quantity region corresponds to a "proper quantity region" in the claims, and an area of the SAP-proper-quantity region corresponds to "a value indicating the size of a proper quantity region" in the claims.

It is to be noted that a program for executing the extracting process and a program for executing the pass/fail determination process are pre-stored in the memory. Then, the processor reads out and executes these programs and thus the image processing section 56 operates as an "extraction processing section" which executes an extraction process and a "pass/fail determination processing section" which executes a pass/fail determination process. Hereinafter, the extraction process and the pass/fail determination process will be described in detail.

Figure 5:
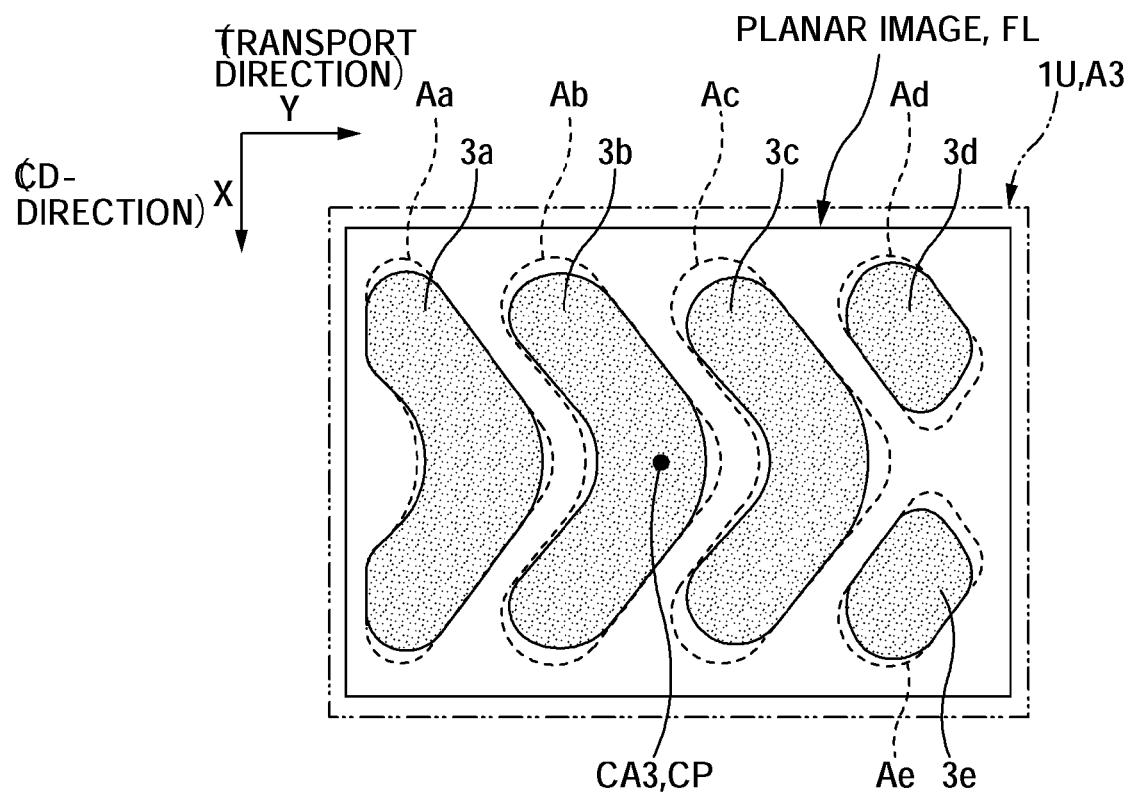
FIG. 5 is an explanatory diagram of a planar image of the absorbent sheet-like member 1 imaged with a CCD camera 52.

First, before explaining the extraction process, the planar image and the planar image data will be described. FIG. 5 is an explanatory diagram of the planar image.

The planar image is imaged, for example, with the CD-direction being an X-direction and the transport direction being a Y-direction. Also, the planar image is imaged such that the five deposited bodies 3a-3e of the absorbent body 3 are in a single image, and, in other words, an inner side of a frame FL having a rectangular contour and surrounding the absorbent body 3 is imaged as an imaging range. It is to be noted that, in order to facilitate the understanding of the imaging range, the single-cut sheet-like product 1U of the absorbent sheet-like member 1 is indicated virtually with a dash-dot-dot line in FIG. 5. Further, in FIG. 5, the SAP deposition target regions Aa-Ae are also virtually indicated with broken lines. Further, in FIG. 5, for the sake of explanation, the deposited bodies 3a-3e are indicated as being exposed from the surface, but the deposited bodies 3a-3e are in practice covered with the back face web 7 and the deposited bodies 3a-3e can be seen through the back face web 7. This is the same for FIGS. 6A, 7A and 7B to be described later.

The imaged planar image is an aggregate of a plurality of pixels that are arranged in a lattice like manner at a predetermined pitch in accordance with predetermined resolutions in the X-direction and the Y-direction, respectively. In other words, the planar image includes a plurality of arrays of pixels arranged at a predetermined pitch in the Y-direction and each array of pixels includes a plurality of pixels linearly aligned at a predetermined pitch. The planar image data has color information corresponding to each of the pixels. For example, when the planar image data is grey scale, each pixel has only its brightness as the color information. Then, in such a case, in a configuration of an example of FIG. 1 in which the reflected light is received, each pixel corresponding to the region where SAP exist becomes bright and thus the brightness of those pixels has a higher value, whereas, each pixel corresponding to the region where SAP does not exist becomes dark and thus the brightness of those pixels has a lower value. Also, even for the pixel corresponding to the region where the SAP exists, the brightness of the pixel changes in accordance with a magnitude of the basis weight ($g/m^2$) of the SAP. In other words, the brightness of a pixel is higher where it corresponds to a portion where the basis weight ($g/m^2$) of SAP is smaller, when compared to a pixel corresponding to a region where the basis weight of SAP is larger. Therefore, as will be described later, by focusing on the pixel whose brightness is greater than or equal to a predetermined value, a pixel that is formed by imaging a section where SAP is deposited with a predetermined basis weight or more can be extracted. It is to be noted that the following description is made by considering that the planar image data is grey scale data.

Figure 6A:
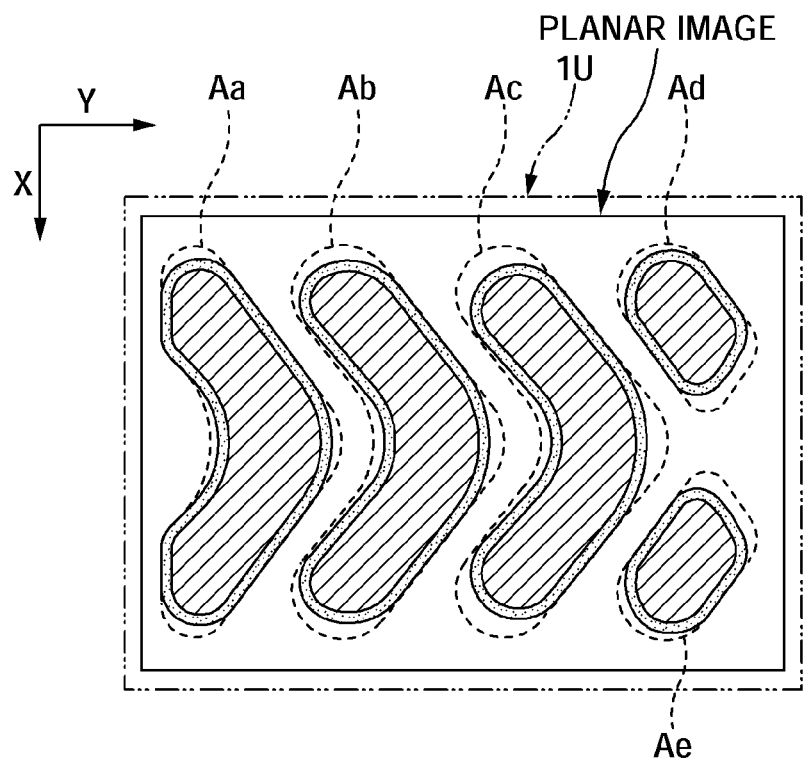
FIG. 6A is a diagram illustrating a planar image before a binary process and FIG. 6B is a diagram illustrating a state after having performed the binary process on the planar image, i.e., a state after extracting a SAP adequate amount region.
Figure 6B:
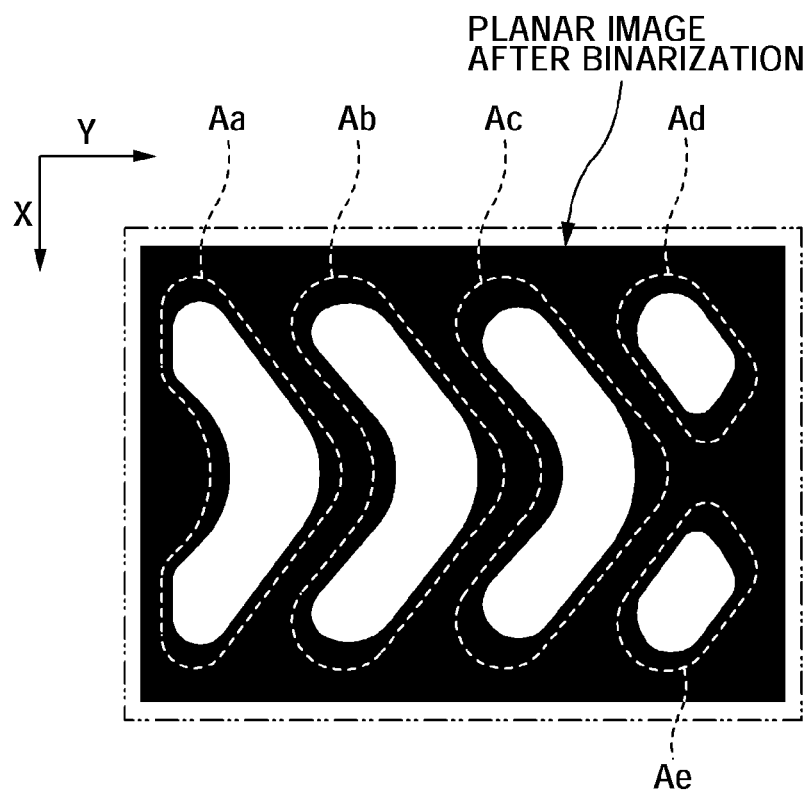

FIGS. 6A and 6B are explanatory diagrams of an extracting process. FIG. 6A shows a planar image before a binarizing process and FIG. 6B shows a state after performing the binarizing process on the planar image, i.e., a state after having extracted the SAP-proper-quantity region. In FIGS. 6A and 6B, the SAP deposition target regions Aa-Ae are virtually indicated with broken lines and in FIG. 6A, a region where SAP is imaged as being deposited in the planar image is indicated with dot-shaded area and, within the region, a region where SAP of the specified basis weight or more is imaged is indicated with hatchings.

In the binarizing process, a predetermined extraction threshold is used. A pixel having a brightness greater than or equal to the extraction threshold is, for example, assigned to white, whereas, a pixel having a brightness less than the extraction threshold is, for example, assigned to black. This is performed for all the pixels in the planar image data, and thus the SAP-proper-quantity region indicated with hatchings in FIG. 6A, i.e., a region in which there is SAP of the specified basis quantity or more, is extracted as a region including a plurality of white pixels, as indicated in FIG. 6B as a white area.

Here, the above-mentioned extraction threshold is a fixed value that is pre-stored in the memory. In order to ensure that, in the region in which SAP is imaged, a pixel in the region where SAP of a specific basis weight or more can be specifically assigned to white, the extraction threshold value is, for example, derived in an empirical manner in the production line as follows. First, several sheets of samples of the absorbent sheet-like member 1 on which SAP is deposited with the above-mentioned specified basis weight are prepared. Then, these samples are imaged with the above-mentioned CCD camera 52 of the inspecting apparatus 50 and the brightness is obtained for each sample. By calculating an average value of the brightness of all the samples, the above-mentioned extraction threshold is determined as the average value. It is to be noted that in order to more securely assign the pixel of the imaging region with the specified basis weight or more to white, a value that is larger than the value of the average value of the brightnesses obtained by the above-mentioned method by a predetermined safety factor may be set as the above-mentioned extraction threshold. Then, a safer determination can be made at the time of the pass/fail determination process.

However, the method of determining this extraction threshold is not limited thereto and may be determined as follows. First, samples of the absorbent sheet-like member 1 with different bases weights (g/m$^2$) with a plurality of levels are prepared and these samples are imaged with the above-mentioned CCD camera 52, and the brightness is determined for each sample. Then, the data of the obtained brightness and the basis weight is plotted to create a graph of the relationship between the brightness and the basis weight, and a value of the brightness corresponding to the above-mentioned specified basis weight is read from this graph and the above-mentioned extraction threshold is obtained. A concrete value for the specific basis weight may be, for example, any value between 100 and 500 g/m$^2$.

Then, the image processing section 56 moves over to the pass/fail determination process. In the pass/fail determination process, first, an area of the SAP-proper-quantity region on the planar image is derived. Here, the planar size of the pixel is known in advance based on a resolution in each of the X- and Y-directions. Therefore, the area of the SAP-proper-quantity region can be calculated by multiplying the planar size of the pixel by the number of pixels that is the number of pixels extracted as the SAP-proper-quantity region.

Then, the image processing section 56 compares the size of the area of the calculated SAP-proper-quantity region and the pass/fail determination threshold which is pre-stored in the memory. Then, in a case where it is greater than or equal to the pass/fail threshold, acceptable product information is applied to the single-cut sheet-like product 1U of the absorbent sheet-like member 1 corresponding to the planar image, whereas, in the case where it is less than the pass/fail threshold, defective product information is applied. The pass/fail threshold is set in advance as described in the following. First, a total value of the areas on the planar image of the five SAP deposition target regions Aa-Ae specified by the deposition pattern PT is derived, and an arbitrary value is selected from a range of 50%-99% of the total value and set as a pass/fail determination threshold.

Depending on the case, instead of the pass/fail determination using the area as described above, the pass/fail determination may be performed using the rate of area or the number of pixels. Here, the rate of area is a value obtained by dividing the area of the SAP-proper-quantity by the total value of areas of the above-mentioned five SAP deposition target regions Aa-Ae. Therefore, an arbitrary value is selected as the pass/fail determination threshold for this case from, for example, a range of 0.50-0.99. Then, the rate of area is compared with the above-mentioned pass/fail determination process, and based on the result of comparison, either the acceptable product information or the defective product information is applied to the absorbent sheet-like member 1.

On the other hand, when the pass/fail determination is performed using the number of pixels, the image processing section 56 counts the number of pixels belonging to the SAP-proper-quantity region. Then, the counted number of pixels is compared with the pass/fail determination threshold expressed in the number of pixels, and based on the result of comparison, either the acceptable product information or the defective product information is applied to the single-cut sheet-like product 1U of the absorbent sheet-like member 1 corresponding to this planar image. It is to be noted that the pass/fail determination threshold in this case is, for example, pre-set in a manner described below. First, a sum of the pixels belonging to the five SAP deposition target regions Aa-Ae on the planar image is derived, and then an arbitrary value is selected from a range of numerical values of 0.50 times to 0.99 times the sum and set as the pass/fail determination threshold.

Preferably, the above-mentioned extraction process and the pass/fail determination process are performed for each SAP deposition target region Aa, Ab . . . Ae. In this manner, since the pass/fail determination can be performed for each of the SAP deposition target regions Aa, Ab . . . Ae, a final pass/fail determination of the absorbent body 3 can be made by taking into consideration whether or not there is the bias of a partially deposited state, and thus a more accurate inspection result information can be obtained. Also, in a case where the pass/fail determination result of one of the SAP deposition target regions Aa, Ab . . . Ae indicates a defect determination, it is possible to instantly recognize which of the five recessed sections 24a-24e of the mold 24 of the rotating drum unit 20 is abnormal; then, an object requiring maintenance can be easily found and thus the efficiency of maintenance can be improved. This will be described in detail below.

Figure 7A:
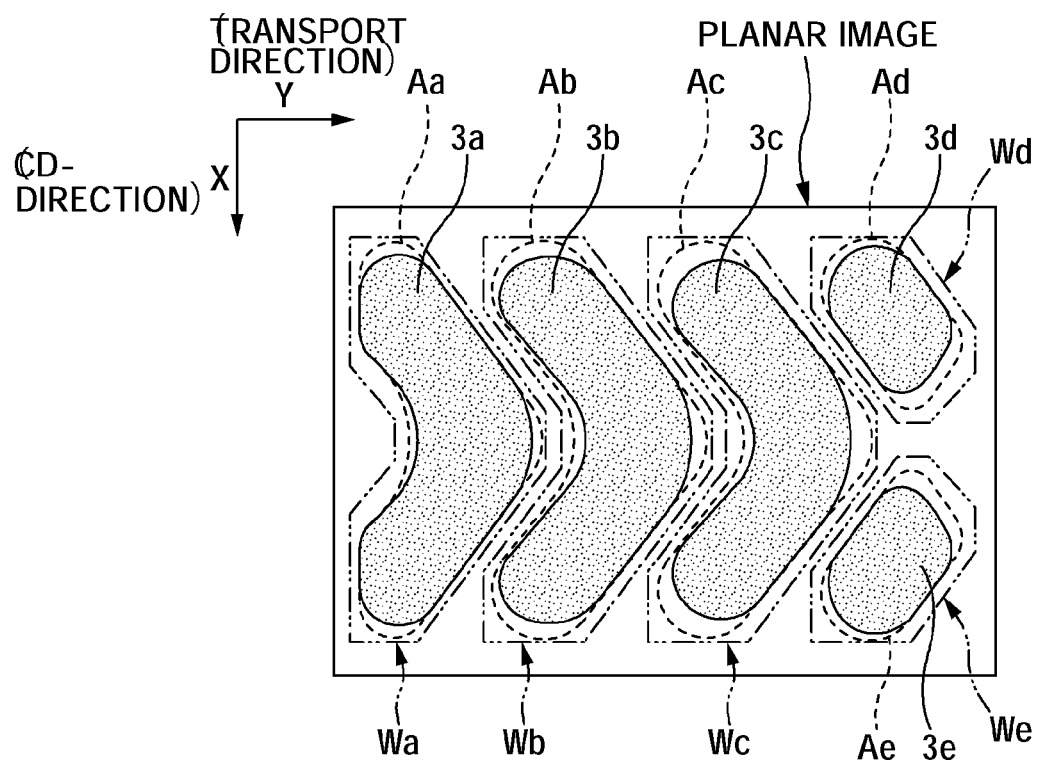
FIG. 7A is a diagram illustrating an example of an explanatory diagram of inspecting windows Wa, Wb, Wc, Wd and We and, FIG. 7B is another explanatory diagram illustrating inspecting windows Wa, Wb, Wc and Wf.

FIG. 7A shows an image diagram of the imaged planar image. In this example, the image processing section 56 uses inspection windows Wa, Wb, Wc, Wd and We during the extracting process. The inspection windows Wa, Wb, Wc, Wd and We are tools that subdivide and limit regions referenced in the planar image; in other words, during the extracting process, it can be configured in such a manner that it refers to the pixels in the inspection windows Wa-We only, and not to refer to pixels outside the inspection windows Wa-We.

It is to be noted that the referencing of the pixels limited within such inspection windows Wa-We can be achieved in the following manner. First, each of the pixels in the planar image has X-, Y-coordinates applied thereto and the X-, Y-coordinates are stored in the memory. The image processing section 56 can access color information of the pixel belonging to the inspection windows Wa-We by specifying these X-, Y-coordinates. Accordingly, by pre-storing the data of the X-, Y-coordinates of the pixel that should be located within the inspection windows Wa-We in the memory, the referencing of the pixels limited to those within the above-mentioned inspection windows Wa-We can be achieved.

These inspection windows Wa, Wb . . . We are prepared for the SAP deposition target regions Aa, Ab, . . . Ae, respectively. In this example, since the absorbent body 3 has five SAP deposition target regions Aa, Ab, . . . Ae, five inspection windows Wa-We are correspondingly prepared. Also, the contour of each of the inspection windows Wa-We is provided as a shape which is substantially similar to the shape of the contours of the corresponding SAP deposition target regions Aa, Ab, . . . Ae. In this example, since the contour of each of the three SAP deposition target regions Aa, Ab and Ac is V-shaped, the inspection windows Wa, Wb and We each has a V-shaped contour. On the other hand, since the remaining two SAP deposition target regions Ad and Ae has a shape that is divided in the width direction with the bent portion of the V-shape being removed, the inspection windows Wd and We are provided with a corresponding contour shape. Also, the planar size of the inspection windows Wa, Wb . . . We on the planar image is set so as to be slightly larger than an image of the corresponding SAP deposition target regions Aa, Ab, . . .

Ae, so as to be capable of surrounding the outside of the image of the corresponding SAP deposition target regions Aa, Ab, . . . Ae.

Then, with such a configuration of the inspection windows Wa-We, in the extracting process, the SAP-proper-quantity region is extracted for each inspection window Wa, Wb . . . We and thus an area of the SAP-proper-quantity region is calculated for each of the inspection windows Wa, Wb . . . We.

Then, in the following pass/fail determination process, a pass/fail determination result is obtained for each of the inspection windows Wa, Wb . . . We using the pass/fail determination threshold that is pre-set for each of the inspection windows Wa, Wb . . . We.

Here, the pass/fail determination threshold is an area on the planar image of the SAP deposition target regions Aa, Ab, . . . Ae corresponding to the inspection windows Wa, Wb . . . We, respectively, and in this example, since there are five SAP deposition target regions Aa, Ab, . . . Ae, there are five pass/fail determination thresholds. Therefore, by comparing the area of each of the SAP-proper-quantity regions extracted in each of the inspection windows Wa, Wb . . . We with the pass/fail determination threshold associated with the relevant inspection windows Wa, Wb . . . We, in a case where the area of the SAP-proper-quantity region is greater than or equal to the pass/fail determination threshold, a temporary acceptable product information is applied to the relevant SAP-proper-quantity region as primary determination information. On the other hand, conversely, in a case where it is less than the determination threshold, temporary defective product information is applied as primary determination information. Then, such a pass/fail determination process is performed for all the five inspection windows Wa, Wb . . . We, and finally, in a case where the temporary acceptable product information is applied to all the SAP-proper-quantity regions, acceptable product information is applied to the single-cut sheet-like product 1U of the absorbent sheet-like member corresponding to this planar image as secondary determination information, and this information is sent to the downstream process as inspection result information. In a case where any one of the five SAP-proper-quantity regions has temporary defective product information applied thereto, defective product information is applied to the single-cut sheet-like product 1U of the absorbent sheet-like member 1 corresponding to the planar image as secondary determination information, and this information is sent to the downstream process as inspection result information.

Figure 7B:
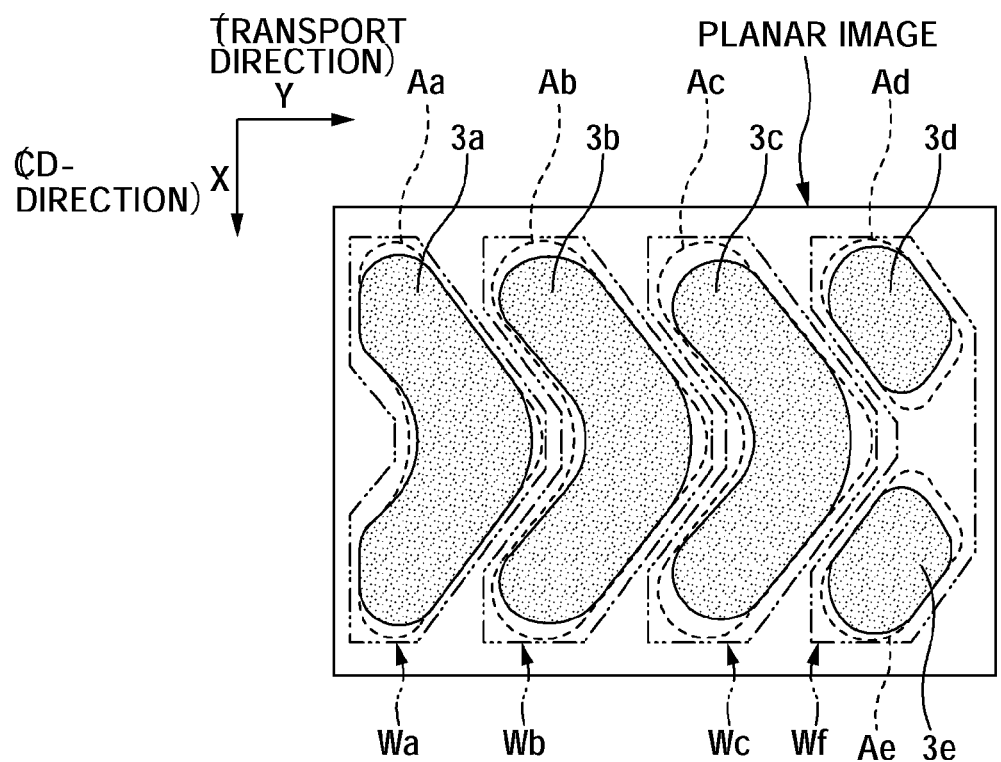

It is to be noted that in the above-mentioned example, the inspection windows Wa, Wb . . . We, are respectively set for the five SAP deposition target regions Aa, Ab, . . . Ae, but it is not limited thereto. A different number of inspection windows may be provided compared to the number of SAP deposition target regions. For example, the inspection windows Wa, Wb, and Wc may be provided for each of the SAP deposition target regions Aa, Ab and Ac, respectively, for some of the SAP-proper-quantity regions Aa, Ab and Ac, and for the remaining couple of SAP deposition target regions Ad and Ae, a single inspection window Wf of a size that surrounds both of these SAP deposition target regions Ad and Ae may be provided. FIG. 7B illustrates an example of an explanatory diagram thereof. In the example of FIG. 7B, with respect to the SAP deposition target regions Aa, Ab and Ac having bent portions, the inspection windows Wa, Wb, Wc are individually provided for the SAP deposition target regions Aa, Ab and Ac, respectively, whereas, with respect to the SAP deposition target regions Ad and Ae from which the bent portions have been removed, a single inspection windows Wf may be provided that surrounds both of the regions Ad and Ae, respectively. In such a case, in the inspection windows Wf, of course, the extracting process is performed at once without distinguishing the two SAP deposition target regions Ad and Ae, and, as a pass/fail determination threshold for use in the pass/fail determination process, an arbitrary value is selected from a range of 50%-99% of the total value of the areas on the planar image of the two SAP deposition target regions Ad and Ae.

In the above-mentioned embodiment, grey scale data was indicated as an example of planar image data in which the color information of each pixel has brightness only, but it is not limited thereto. For example, it may be color image data in which the color information of each pixel has brightness, hue and saturation. In such a case, a color binarization process may be performed as a binarizing process in the above-mentioned extracting process.

The color binarizing process is a process in which a pixel having particular color information is extracted from the color image data of a planar image. Here, as has been described above, the color information has their elements, i.e., brightness, hue and saturation, each expressed in a numerical value. Therefore, for each of brightness, hue and saturation, with the numerical value ranges of color information of the pixels to be extracted being set as the extraction thresholds into the memory of the image processing section 56, the image processing section 56 can extract the pixel of the set color information from the planar image.

In other words, with the above-mentioned three numerical value ranges of the extraction thresholds being pre-set based on color which is specific to the region in the planar image in which SAP of specified basis weight or more is imaged, the image processing section 56 refers to the color information of each pixel in the planar image recorded in the planar image data, and assigns a pixel satisfying all three of the numerical value ranges of the above-mentioned extraction thresholds to a white pixel and assigns the pixel that does not satisfy them to a black pixel. This assigning operation is performed for all pixels in the planar image data and thus the SAP-proper-quantity region is extracted as a region of white pixels. With such a method, since the SAP-proper-quantity region is extracted based on the above-mentioned specific color, an extracting accuracy can be improved. Since the matters other than those described above are the same as the matters that have been already described by taking grey scale as an example, the explanation thereof will be omitted.

It is to be noted that, in the description above, the color of the front face web 5, the back face web 7, the adhesive agent and the SAPs was not explained, but their color is typically white. However, it is not limited thereto, and, for example, at least one of the front face web 5, the back face web 7, the adhesive agent and the SAPs may be colored with a color other than white. Even in such a case, with a color binarizing process, by the setting of the above-mentioned three numerical value ranges that are extraction thresholds, the SAP-proper-quantity region can be extracted from the planar image without any problem.

Other Embodiments

In the embodiments mentioned above, the embodiments of the present invention have been discussed. However, the above-mentioned embodiments are provided for the purpose of facilitating the understanding of the present invention only and do not give any limitation to the present invention. It goes without saying that any modifications and improvements to the present invention can be made without departing from the spirit of the invention and the present invention includes its equivalents. For example, the modifications described below are possible.

In the above-mentioned embodiments, superabsorbent polymer (SAP) is illustrated as an example of a liquid absorbent particulate, but it is not limited to the super absorbent polymer as long as it is a particulate having the property of not releasing liquid which has been absorbed by swelling.

In the above-mentioned embodiments, the front face web 5 and the back face web 7 with the absorbent body 3 interposed between them are illustrated as an example of the absorbent sheet-like member 1, but it is not limited thereto, and for example, the back face web 7 may be omitted. In other words, the absorbent sheet-like member 1 may include the front face web 5 and the absorbent body 3 in which SAP is deposited with the deposition pattern PT on one side of the front face web 5.

In the above-mentioned embodiments, it has not been described that the planar image after the binarizing process of FIG. 6B is displayed on a screen based on the planar image data after the binarizing process, but such a configuration is of course possible. In other words, the image processing section 56 has an appropriate monitor, not shown, which is provided as an accessory. Then, the planar image of FIG. 6B may be displayed on the monitor in accordance with planar image data produced by assigning each pixel relating to the planar image data to white or black based on the extraction threshold, and may be used in supporting the inspection operation by an operator of the production line.

In the above-mentioned embodiments, as shown in FIG. 6, (A), V-shaped inspections windows are illustrated as examples of the inspection windows Wa, Wb and Wc, and this is because the contour of the corresponding SAP deposition target regions Aa, Ab and Ac are V-shaped. Therefore, depending on the shape of contour of the SAP deposition target region, the shape of the contour of the corresponding inspection window may be modified. For example, if the shape of contour of the SAP deposition target region has an hourglass shape, in order to surround the outside of this image, the shape of the contour of the corresponding inspection window on the planar image may be an hourglass shape having a planar size that is slightly larger than the image of the SAP deposition target region.

In the above-mentioned embodiments, the adhesive agent is applied only on the back face web 7. In other words, the adhesive agent is applied on substantially the entire region of a surface of the back face web 7 that is to be overlapped on the front face web 5 and the adhesive agent is not applied on the front face web 5, but it is not limited thereto. For example, the adjective agent may be applied on substantially the entire region of a surface of the front face web 5 instead of the back face web 7 and, further, the adhesive agent may be applied on substantially the entire region of each surface of the back face web 7 and the front face web 5 to be overlapped.

In the above-mentioned embodiments, the front face web 5 and the back face web 7 are temporarily joined with the adhesive agent, but it is not limited thereto, and the adhesive agent may be applied to neither the front face web 5 nor the back face web 7. In such a case, the temporary joining is not performed and only the final joining by the heat sealing unit 40 is performed.

In the above-mentioned embodiments, grey scale data is used as the planar image data, and brightness is used as the threshold value in extracting, but it is not limited thereto. For example, color image data may be used as the planar image data, and in that case, hue or saturation may be used instead of brightness as the threshold value in extracting, such that two selected from brightness, hue and saturation may be selected and used as a threshold value in extracting.

REFERENCE SIGNS LIST 1 absorbent sheet-like member, 1U single-cut sheet-like product,
3 absorbent body,
3a deposited body, 3b deposited body, 3c deposited body,
3d deposited body, 3e deposited body,
5 front surface web (continuous web),
7 back surface web (another continuous web),
10 manufacturing apparatus,
20 rotating drum apparatus,
22 rotating drum, 22a outer peripheral surface,
24 mold,
24a recessed section, 24b recessed section, 24c recessed section,
24d recessed section, 24e recessed section,
26 suction hole,
30 SAP supplying apparatus, 35 adhesive applying apparatus,
40 heat sealing apparatus, 42 upper roll, 42a outer peripheral surface, lower roll,
50 inspecting apparatus, 52 camera (imaging process section),
54 illuminating member,
56 image processing section (extracting process section, defect determination process section),
SAP superabsorbent polymer (liquid absorbent particulate),
PT deposited pattern,
Aa SAP deposition target region (particulate deposition target region),
Ab SAP deposition target region (particulate deposition target region),
Ac SAP deposition target region (particulate deposition target region),
Ad SAP deposition target region (particulate deposition target region),
Ae SAP deposition target region (particulate deposition target region),
A3 region, CA3 center of plane, CP center of plane,
FL frame,
P5 supplying position, PS imaging position,
Wa inspection window, Wb inspection window, We inspection window,
Wd inspection window, We inspection window, Wf inspection window,
N deposited-body-free portion, ENC enclosed section,
G40 roll gap,
C22 horizontal axis, C42 horizontal axis, C44 horizontal axis,
Tr22 circumferential track

The invention claimed is:

1. An inspecting apparatus that inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting apparatus comprising:

an imaging process section which is adapted to image, from one side of a surface of the absorbent sheet-like member, a region on the absorbent sheet-like member where the absorbent body is expected to exist, and that is adapted to produce data relating to a planar image of the region as planar image data of the absorbent body;

an extracting process section which is adapted to extract a proper quantity region from the planar image by performing a binarization process on the produced planar image data based on a threshold value, the proper quantity region being an imaged region in which the liquid absorbent particulate is of a specified amount or more; and a pass/fail determination process section that is adapted to perform a pass/fail determination process based on a value indicating a size of the proper quantity region, wherein the inspecting apparatus is arranged downstream of a heat sealing unit, the absorbent sheet-like member is provided with a plurality of particulate deposition target regions for each absorbent body based on the deposition pattern, the particulate deposition target regions being arranged discretely in an island-like manner, each of the particulate deposition target regions being a region in which the liquid absorbent particulate is expected to exist, the extracting process section sets respective inspection windows for at least some of the plurality of particulate deposition target regions and is adapted to extract the proper quantity region for each inspection window, the inspection window having a contour corresponding to a contour of the particulate deposition target region, and the pass/fail determination process section is adapted to perform a pass/fail determination of the absorbent body based on an area as a value indicating the size of the proper quantity region which has been extracted for each inspection window, the pass/fail determination process section:

compares the area of each of the proper-quantity regions extracted in each of the inspection windows with a pass/fail determination threshold associated with the inspection windows;

in a case where the area of the proper-quantity region is greater than or equal to the pass/fail determination threshold, applies temporary acceptable product information to the proper-quantity region as primary determination information;

in a case where the area of the proper-quantity region is less than the pass/fail determination threshold, applies temporary defective product information as the primary determination information;

in a case where the temporary acceptable product information is applied to all the proper-quantity regions, applies acceptable product information to a single-cut sheet-like product of the absorbent sheet-like member corresponding to the planar image as secondary determination information, and in a case where any one of the proper-quantity regions has temporary defective product information applied thereto, applies defective product information to the single-cut sheet-like product of the absorbent sheet-like member corresponding to the planar image as secondary determination information.

2. An inspecting apparatus which inspects an absorbent sheet-like member relating to an absorbent article according to claim 1, wherein, the extracting process section sets an inspection window for each of the particulate deposition target regions and is adapted to extract the proper quantity region for each inspection window, the inspection window having a contour corresponding to a contour of the particulate deposition target region, and the pass/fail determination process section is adapted to perform a pass/fail determination of the absorbent body based on a value indicating the size of the proper quantity region which has been extracted for each inspection window.

3. An inspecting apparatus which inspects an absorbent sheet-like member relating to an absorbent article according to claim 1, wherein, the extracting process section has a numerical value for at least one of hue, brightness and saturation, that serve as the threshold value, and the extracting process section is adapted to extract the proper quantity region from the planar image by performing a binarization process on the planar image data based on the threshold value.

4. An inspecting apparatus which inspects an absorbent sheet-like member relating to an absorbent article according to claim 3, wherein the planar image data is grey scale data.

5. An inspecting apparatus which inspects an absorbent sheet-like member relating to an absorbent article according to claim 4, wherein the extracting process section has a numerical value for brightness, that serves as the threshold value.

6. An inspecting apparatus which inspects an absorbent sheet-like member relating to an absorbent article according to claim 1, wherein, the planar image data is color image data, the extracting process section has numerical value ranges for hue, brightness and saturation, respectively, that serve as the threshold value, and the extracting process section is adapted to extract the proper quantity region from the planar image by performing a color binarization process on the planar image data based on the threshold value.

7. An inspecting apparatus which inspects an absorbent sheet-like member relating to an absorbent article according to claim 6, wherein, the absorbent sheet-like member has another continuous web that is overlaid on the continuous web so as to sandwich the absorbent bodies in a thickness direction, and the continuous webs are integrally joined with each other, at least in a region other than the particulate deposition target region and the liquid absorbent particulate is enclosed between the continuous webs due to the joining at the region.

8. An inspecting apparatus which inspects an absorbent sheet-like member relating to an absorbent article according to claim 7, wherein, one of the group including the continuous web, the other continuous web and the liquid absorbent particulate, is colored with a color other than white, and the imaging process section is adapted to receive reflected light from the region of the absorbent sheet-like member where the absorbent body is expected to exist, and images the region.

9. An inspecting apparatus which inspects an absorbent sheet-like member relating to an absorbent article according to claim 1, wherein, the planar image data is produced for each of the absorbent bodies by imaging the planar image for each of the absorbent bodies.

10. An inspecting method which inspects whether or not a liquid absorbent particulate is deposited with a predetermined deposition pattern on an absorbent sheet-like member, the absorbent sheet-like member having a continuous web and a plurality of absorbent bodies, the continuous web being transported along a transport direction, the absorbent bodies being formed on one surface of the continuous web in a spaced apart manner in the transport direction, each absorbent body including the liquid absorbent particulate as a main material, the inspecting method comprising:

imaging, from one side of a surface of the absorbent sheet-like member, a region on the absorbent sheet-like member where the absorbent body is expected to exist, and producing data relating to a planar image of the region as planar image data of the absorbent body;

extracting a proper quantity region from the planar image by performing a binary process on the produced planar image data based on a threshold value, the proper quantity region being an imaged region In which the liquid absorbent particulate is of a specified amount or more; and performing a pass/fail determination process based on a value indicating the size of the proper quantity region, wherein the inspecting method further comprising:

arranging an inspecting apparatus downstream of a heat sealing unit, the inspecting apparatus inspecting whether or not the liquid absorbent particulate is deposited with the predetermined deposition pattern on the absorbent sheet-like member, providing the absorbent sheet-like member with a plurality of particulate deposition target regions for each absorbent body based on the deposition pattern, the particulate deposition target regions being arranged discretely in an island-like manner, each of the particulate deposition target regions being a region in which the liquid absorbent particulate is expected to exist, setting respective inspection windows for at least some of the plurality of particulate deposition target regions and extracting the proper quantity region for each inspection window, the inspection window having a contour corresponding to a contour of the particulate deposition target region, performing a pass/fail determination of the absorbent body based on an area as a value indicating the size of the proper quantity region which has been extracted for each inspection window, comparing the area of each of the proper-quantity regions extracted in each of the inspection windows with a pass/fail determination threshold associated with the inspection windows, in a case where the area of the proper-quantity region is greater than or equal to the pass/fail determination threshold, applying temporary acceptable product information to the proper-quantity region as primary determination information, in a case where the area of the proper-quantity region is less than the pass/fail determination threshold, applying temporary defective product information as the primary determination information, in a case where the temporary acceptable product information is applied to all the proper-quantity regions, applying acceptable product information to a single-cut sheet-like product of the absorbent sheet-like member corresponding to the planar image as secondary determination information, and in a case where any one of the proper-quantity regions has temporary defective product information applied thereto, applying defective product information to the single-cut sheet-like product of the absorbent sheet-like member corresponding to the planar image as secondary determination information.

\* \* \* \* \*